United States Patent [19]

Ragi et al.

[11] Patent Number: 5,625,112

[45] Date of Patent: Apr. 29, 1997

[54] METHOD OF INDIRECT HEAT EXCHANGE FOR TWO PHASE FLOW DISTRIBUTION

[75] Inventors: Elias G. Ragi, Williamsville; Thomas J. Godry, Tonawanda, both of N.Y.

[73] Assignee: UOP, Des Plaines, Ill.

[21] Appl. No.: 530,982

[22] Filed: Sep. 20, 1995

Related U.S. Application Data

[62] Division of Ser. No. 174,510, Dec. 28, 1993, Pat. No. 5,531,266.

[51] Int. Cl.[6] .................................. C07C 2/62; C07C 2/56
[52] U.S. Cl. ............................. 585/709; 585/715
[58] Field of Search ......................... 585/709, 715

[56] References Cited

U.S. PATENT DOCUMENTS

| | | | |
|---|---|---|---|
| 1,358,050 | 11/1920 | Audianne | 165/174 |
| 2,099,186 | 11/1937 | Anderegg | 165/174 X |
| 2,707,868 | 5/1955 | Goodman | 165/174 X |
| 4,572,287 | 2/1986 | Allo et al. | 165/115 X |
| 4,607,689 | 8/1986 | Mochida et al. | 165/174 |
| 4,769,511 | 9/1988 | O'Neill | 585/715 |
| 5,091,075 | 2/1992 | O'Neill et al. | 208/134 |
| 5,150,749 | 9/1992 | Bergmann et al. | 165/115 |

FOREIGN PATENT DOCUMENTS

| | | | |
|---|---|---|---|
| 567362 | 2/1957 | Italy | 165/174 |
| 558510 | 1/1975 | Switzerland | 165/174 |
| 27198 | 9/1898 | United Kingdom | 165/158 |
| 635793 | 4/1950 | United Kingdom | 165/174 |

*Primary Examiner*—Glenn A. Caldarola
*Assistant Examiner*—Walter D. Griffin
*Attorney, Agent, or Firm*—Thomas K. McBride; John G. Tolomei

[57] ABSTRACT

A method and apparatus for indirectly heating a mixed phase stream by contact with a boiling surface located on the inside of the plurality of heat exchange tubes. Improved vaporization of the stream is achieved by equalizing the liquid distribution and the ratio of liquid and vapor entering each tube to overcome poor boiling film heat transfer. The invention uses a means for subdividing the flow entering the heat exchanger into a plurality of streams with each of the divided streams discharging directly into a heat exchange tube. The means for dividing the stream can include baffle arrangements or plugs providing pressure drop at the inlets to the tubes. This method and apparatus is particularly useful in contactors for the sulfuric acid catalyzed alkylation of hydrocarbons.

8 Claims, 4 Drawing Sheets

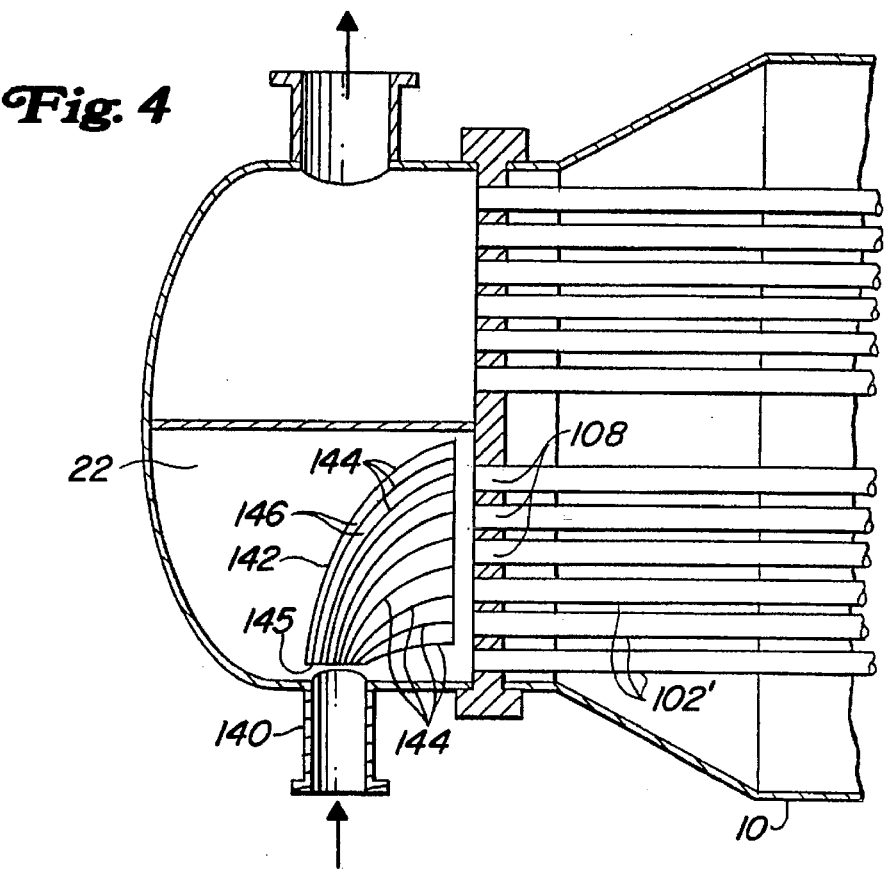
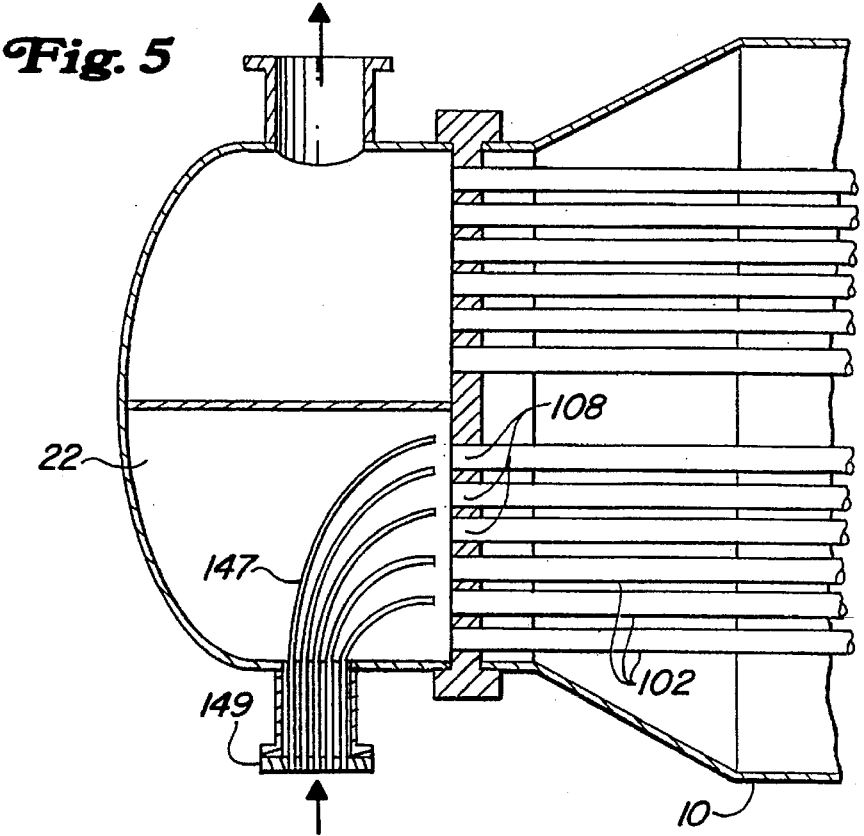

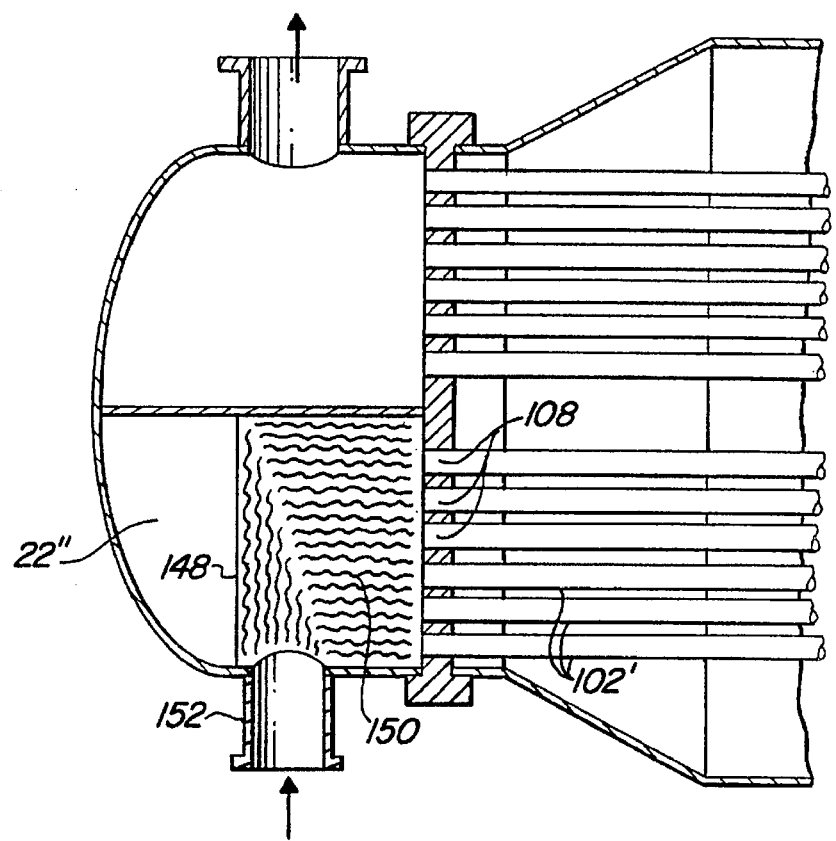
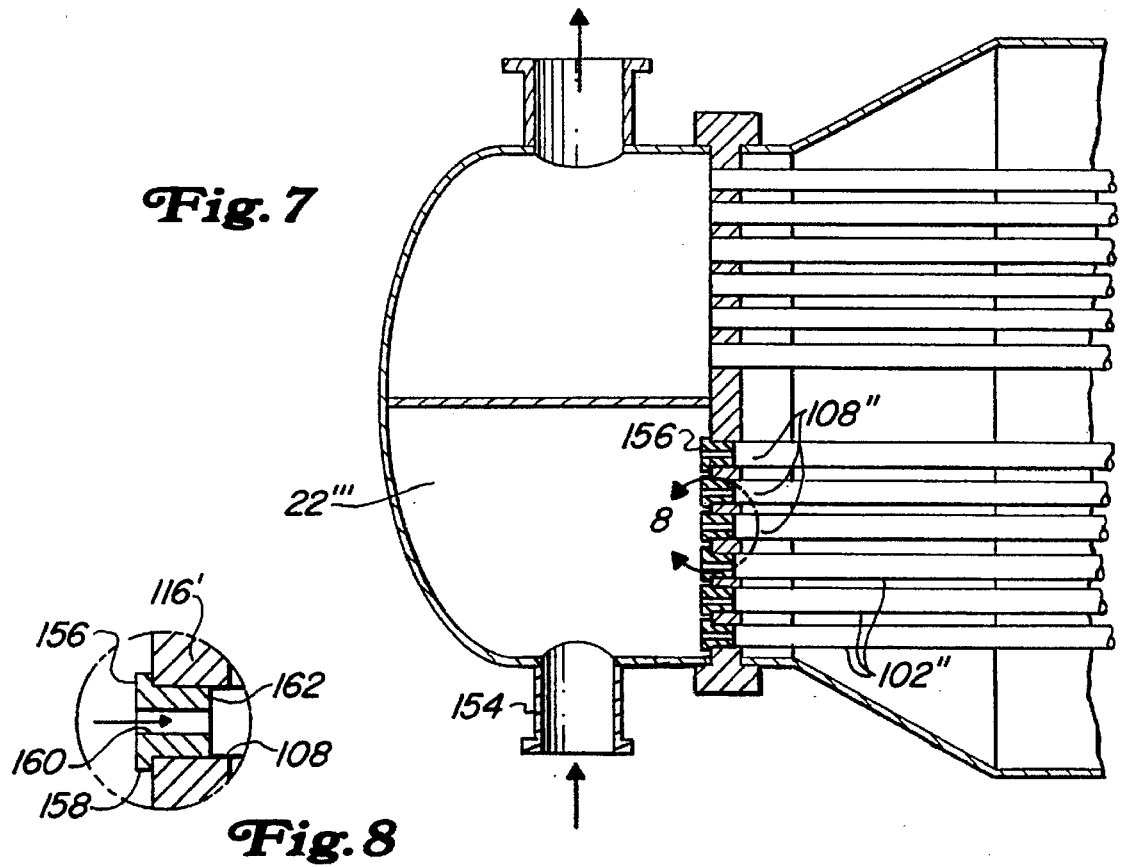

METHOD OF INDIRECT HEAT EXCHANGE FOR TWO PHASE FLOW DISTRIBUTION

CROSS REFERENCE TO RELATED APPLICATION

This application is a divisional application of U.S. Ser. No. 08/174,510, now U.S. Pat. No. 5,531,266, filed Dec. 28, 1993.

FIELD OF THE INVENTION

This invention relates generally to the indirect heat exchange of mixed phase fluids. More specifically, this invention relates to the indirect heat exchange of mixed phase fluids where the mixed phase fluid contacts a boiling surface.

BACKGROUND OF THE INVENTION

The use of enhanced boiling surfaces, and in particular nucleate boiling surfaces to increase the heat transfer film coefficient on boiling side heat transfer surfaces is well-known. U.S. Pat. No. 4,769,511 discloses the use of an enhanced nucleate boiling surface to improve the operation of a process for the alkylation of isoparaffins. The use of nucleate boiling surfaces to improve the operation of heat exchange equipment in the reforming of hydrocarbons is disclosed in U.S. Pat. No. 5,091,075.

Although enhanced boiling surfaces will usually improve the operation of exchangers and the processes in which the indirect heat exchangers operate, it has been unexpectedly found that enhanced boiling surfaces in some boiling applications will provide little or no benefit. The achievement of little or no benefit from the addition of an enhanced boiling surface was difficult to understand. Enhanced nucleate boiling surfaces greatly improve the heat transfer coefficient across the boiling film. An enhanced boiling surface having a porous boiling layer should provide about a ten fold increase in the nucleate boiling film coefficient. The contribution of the enhanced nucleate boiling surface in providing an improvement in overall heat transfer when used in flow boiling on the inside of a tube, of course, depends on the contribution to the heat transfer associated with nucleate boiling across the film and the contribution associated with convection. In some flow boiling applications, as much as 85% of the contribution to the overall heat transfer is attributable to convection. Nevertheless, in such cases even a 15 to 25% contribution of the nucleate boiling film heat transfer coefficient will allow the use of an enhanced boiling surface to demonstrate significant improvements in the overall heat transfer coefficient. Thus as long as their is some vapor generation, the addition of such a surface should provide a significant increase in the overall heat transfer performance. Moreover, in several instances data showed that nucleate boiling surfaces achieved less than a quarter of the tube side boiling heat transfer coefficient predicted by calculation.

A specific case where an enhanced boiling surface in a heat exchanger provided no benefit was in sulfuric acid alkylation process. The basic reaction of this process is the conversion of isobutane and isobutene in the presence of concentrated sulfuric acid to produce iso-octane. This process is well described in U.S. Pat. No. 4,769,511, the contents of which are herein incorporated by reference. In this process, olefins and isoparaffins are mixed on the shell side of a contactor that contains a plurality of tubes for indirect heat exchange. The product of the reaction is an emulsion of sulfuric acid and alkylate products that is decanted in an acid settler to separate a hydrocarbon stream containing the alkylate products from the acid. In a typical operation, the separated hydrocarbon stream undergoes a Joule-Thomson expansion that cools the liquid and generates a substantial amount of vapor. This two phase mixture of hydrocarbon liquid and vapor enters the inside of the heat exchange tubes in the contactor where further vaporization of the hydrocarbon stream removes heat generated by the alkylation reaction taking place on the shell side of the contactor.

It has been surprisingly found that heat transfer tubes coated with an enhanced porous boiling surface on their inside perform at essentially the same heat transfer rates as bare tubes. It was also unexpectedly encountered that tubes having an interior coating with an enhanced boiling surface demonstrated the same dependence on tube side flow rate as tubes with a bare interior wall. Since an enhanced boiling surface will provide a nucleate boiling heat transfer coefficient for the interior of the tube that is approximately ten times greater than that for a bare tube, the failure to observe any increased performance from the addition of the enhanced boiling surface was difficult to understand.

Moreover, it was unexpectedly found that the bare tubes provided heat transfer rates much below those predicted by known heat transfer correlations. This lower than expected performance was in comparison with correlations that account for stratified flow. Thus, the cause of the observed low heat transfer performance has been difficult to understand.

It is an object of this invention to improve the performance of boiling surfaces in mixed phase flow applications.

It is a further object of this invention to provide a method of achieving higher overall heat transfer rates for an enhanced boiling surface relative to a bare tube surface when contacting the tube surfaces with a mixed phase flow.

Another object of this invention is to improve the operation of acid contactors in alkylation processes that use boiling surfaces in multiple tube arrangements.

A further object of this invention is to provide a heat exchanger that advantageously uses an enhanced boiling surface to vaporize a mixed phase stream by indirect heat exchange.

BRIEF DESCRIPTION OF THE INVENTION

This invention is a method for indirectly heating a mixed phase stream by contact with an enhanced boiling surface located on the inside of a plurality of heat exchange tubes to vaporize a portion of the stream. The method equalizes the distribution of liquid and the ratio of liquid and vapor entering each tube to overcome poor boiling film heat transfer. It was discovered that variations in the amount of liquid and vapor entering each tube create stratified two phase flow in some of the tubes. The stratified two phase flow allows liquid to flow along one section of the tube interior and vapor to flow along another. The stratified layer of vapor renders the boiling surface that it occupies ineffective for boiling heat transfer. Only the areas covered by the liquid will have relatively high nucleate boiling heat transfer coefficients. Equalizing the liquid distribution and the liquid and vapor ratios to the plurality of tubes moves the flow regime within the tubes from the undesirable stratified flow to the highly desirable annular flow with centralized mist.

The method and apparatus of this invention uses an inlet chamber that contains means to improve the uniformity of the total liquid distribution and the liquid to vapor ratio of the fluid that enters each tube in a plurality of heat exchange tubes. It is not necessary that the inlet chamber of this method provide completely equal liquid distribution or liquid to vapor ratios to the inlet of each heat exchange tube. The benefits of this invention are achieved by avoiding extreme differences in the liquid distribution and the liquid to vapor ratio entering different heat exchange tubes. It has been found that distributing the liquid in a manner that improves the liquid distribution and evens out the liquid to vapor ratio of the fluid entering each heat exchange tube will provide some improvement in the heat transfer coefficient provided by the boiling surface. Preferably, the division of the fluid entering the inlet chamber will result in the liquid to vapor ratio and the amount of liquid in the fluid at the inlet to the heat exchange tubes varying by no more than 20% and more preferably by no more than 10%. This invention is applicable to fluid streams that enter the inlet chamber as a liquid and are flashed while passing through the inlet chamber or to fluids that enter the inlet chamber in a mixed phase.

Again, it is not essential to this invention that all the inlets of the tubes receive the same amount of liquid or ratio of liquid to vapor. The invention only requires elimination of large variations in the liquid distribution and liquid to vapor ratios at the inlets to the tubes. A number of suitable methods can be employed to distribute the flow to the tubes in a manner that will tend to equalize the total liquid distribution and the liquid to vapor ratios at the inlets to the tubes. Distributors that will divide the stream to the tubes into smaller streams can even out the liquid distribution and the liquid to vapor ratios at the inlets to the tubes. Flow restrictors just ahead of the inlet to the tubes can provide pressure drop that more evenly distributes the flow of fluid to the tubes and helps to maintain a uniform liquid to vapor ratio in all of the tubes.

Accordingly, this invention is in one embodiment a method for indirectly exchanging heat in a shell and tube heat exchange zone by cooling a first fluid stream on the shell side of the heat exchange zone and boiling a second fluid stream on the tube side of the heat exchange zone. The method passes a first stream comprising a first fluid to the shell side of the shell and tube heat exchange zone and cools the first fluid by contact with the outside surface of a plurality of heat exchange tubes. A second stream comprising a second fluid passes through a tube inlet chamber of the heat exchange zone. The tube inlet chamber divides the second fluid into a plurality of mixed phase inlet streams in a manner that equalizes the amount of liquid and the ratio of liquid to vapor of each of the streams. The inlet chamber directs each of the inlet streams into file inlet of one or more of the heat exchange tubes. Contact of the second fluid inside the heat exchange tubes with a boiling surface boils at least a portion of the second fluid liquid phase.

In another embodiment, this invention is a process for alkylating isoparaffinic hydrocarbons with olefinic hydrocarbons in the presence of an acid catalyst. The process includes steps of reacting the isoparaffinic hydrocarbons and olefinic hydrocarbons in the presence of acid catalyst to form alkylate, separating a hydrocarbon mixture into an acid phase and a hydrocarbon phase, reducing the pressure on the hydrocarbon phase to refrigerate and vaporize volatile hydrocarbons and passing the refrigerated hydrocarbon phase into contact with an enhanced boiling surface located on the interior of a plurality of heat exchange tubes. Vaporization of the hydrocarbons in contact with the enhanced boiling surface effects indirect heat exchange to cool the reaction mixture which is in contact with the exterior of the heat exchange tubes. This invention improves the alkylation process by passing the hydrocarbon phase to a tube inlet chamber that supplies the hydrocarbon phase to a plurality of heat exchange tubes and divides the hydrocarbon phase in the chamber into a plurality of inlet streams. The inlet chamber directs each of the inlet streams into the inlet of one or more of the heat exchange tubes. The inlet chamber also divides each of the streams in a manner that equalizes the distribution of liquid and any weight ratio of liquid to vapor for each of the streams.

In another embodiment, this invention is a shell and tube heat exchanger that comprises a plurality of heat exchange tubes containing a boiling surface on the inside of each tube. An inlet chamber communicates a tube side fluid to the inlet of the heat exchange tubes and passes the tube side fluid into the interior of the tubes. An outlet chamber receives the tube side fluid from the interior of the tubes. The apparatus includes means for contacting the outside surface of the tubes with a shell side fluid and means in the inlet chamber for subdividing the tube side fluid into a plurality of inlet streams and directing each of the inlet streams into at least one of the inlets of the heat exchange tubes.

Additional objects, embodiments, and details of this invention are set forth in the following detailed description of the invention.

BRIEF DESCRIPTION OF THE DRAWINGS

FIGS. 4, 5 and 6 illustrate section views of flow distributors that receive a perpendicular flow of fluid from a radially oriented heat exchanger inlet nozzle.

FIG. 7 shows the location of a plurality of plugs in the inlet chamber for distributing flow.

FIG. 8 shows a detail of a plug and the orifice opening defined thereby.

DETAILED DESCRIPTION OF THE INVENTION

Figure 1:
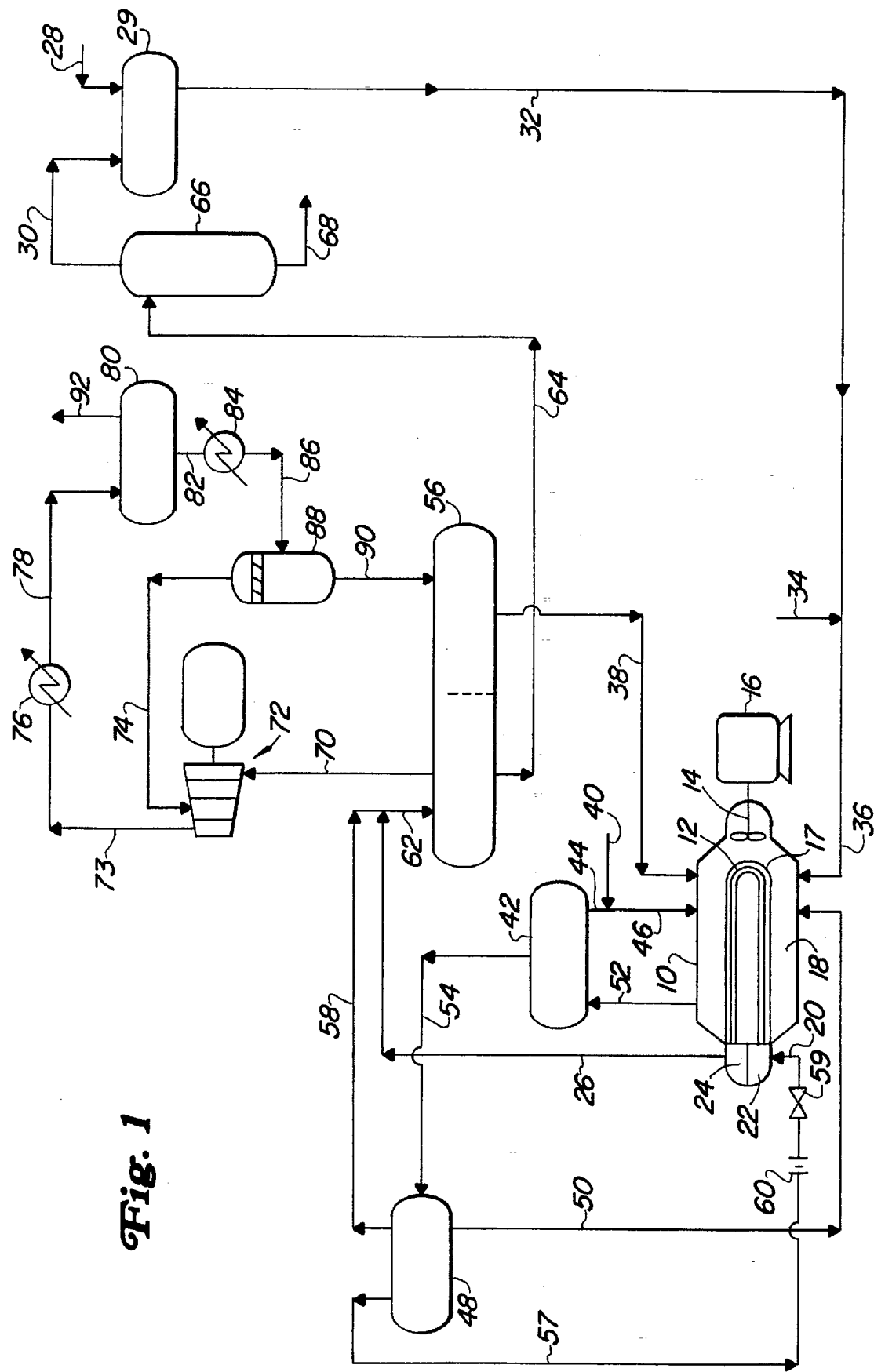
FIG. 1 is a simplified flow diagram of an alkylation process.

The method of this invention is broadly applicable to any process arrangement that partially or fully vaporizes a mixed phase stream on the interior of a plurality of heat exchanger tubes by contact with an enhanced boiling surface to indirectly cool the outer surface of the heat exchange tubes. Fluids that will pass through the interior of the tubes when practicing this invention, include vaporizable liquids with sufficiently low fouling characteristics to permit sustained operation of the enhanced boiling surface. In preferred applications, the fluid will contain hydrocarbons. In order to achieve the benefits of this invention, the fluid passing through the interior of the heat exchange tubes must have a mixed phase. The invention is most useful when the fluid has a high concentration of vapor in the tubes. Preferred concentrations for vapor entering the inlet chamber are in the range of from 0 to 30 wt %. For hydrocarbon streams, such weight percentages of vapor to liquid will typically result in 0 to 99% by volume of vapor. This invention contemplates a 0 percent vapor to liquid ratio where an all liquid stream enters the inlet chamber for the generation of vapor therein.

This invention benefits fluids passing through the heat exchange tubes at both high and low flow rates. It has been found that the ability of this invention to improve heat transfer rates on the boiling side of the heat transfer tube applies to most fluid flow rates normally encountered in typical heat exchanger applications. The fluid flow rate through a heat exchanger in a given process application is determined by pressure drop requirements and utility demands such as compressor usage. For example, in a typical hydrocarbon conversion process application, the flow rate for a tube having a typical outside diameter of from ¾ to 1 inch would fall in a range of from 100 to 400 pounds per hour per tube. This invention will provide improved boiling film heat transfer coefficients at both the high and low end of such a range. It is preferred that the flow rate through tubes having the typical outside diameter is greater than about 150 lbs/hr/tube to avoid a stratified flow regime.

The enhanced boiling surface which may be used on the inside of the heat exchange tubes can consist of any known surface that will provide the desired boiling enhancement over ordinary bare tube walls. Such enhanced boiling surface heat exchange tubes are discussed in, for example, U.S. Pat. Nos. 3,384,154, 3,821,018, 4,064,914, 4,060,125, 3,906,604, 4,216,826 and 3,454,081 all of which are incorporated herein by reference. These enhanced tubes are made in a variety of different ways which are well known to those skilled in the art. For example, such tubes may comprise annular or spiral cavities extending along the tube surface made by mechanical working of the tube. Alternatively, fins may be provided on the surface. So too, the tubes may be scored to provide ribs, grooves, a porous layer and the like.

Generally, the more efficient enhanced tubes are those having a porous layer on the boiling side of the tube which can be provided in a number of different ways well known to those skilled in the art. In one such method, as described in U.S. Pat. No. 4,064,914, the porous boiling layer is bonded to one side of a thermally conductive wall. The porous boiling layer is made of thermally conductive particles bonded together to form interconnected pores.

An essential characteristic of the porous surface layer is the interconnected pores of capillary size, some of which communicate with the outer surface. Liquid to be boiled enters the subsurface cavities through the outer pores and from the subsurface cavities enters interconnecting pores. The liquid is heated by the metal forming the walls of the cavities. At least part of the liquid is vaporized within the cavity and resulting bubbles grow against the cavity walls. Vapor bubbles eventually emerge from the cavity through the outer pores and then rises through the liquid fill over the porous layer for disengagement into the gas space over the liquid fill. Additional liquid flows into the cavity from the interconnecting pores and the mechanism is continuously repeated.

This application is particularly useful in hydrocarbon processes. One particular process to which this invention is especially suited is the acid alkylation of olefins and paraffins to produce iso-octane. A preferred form of the alkylation process uses a sulfuric acid catalyst.

A process for the alkylation of $C_4$ olefins and paraffins is shown in FIG. 1. Referring to FIG. 1, an acid contactor in the form of a reactor shell 10 is equipped with a "U-shaped" heat exchange tube bundle 12. Tube bundle 12 consists of "U-shaped" heat exchange tubes having enhanced boiling surfaces provided on the inside. A propeller or pump impeller 14 is driven to circulate fluid on the shell side of the tube bundle 12. A motor 16 drives the propeller which circulates fluid into the center of a circulation tube 17 and through an annular space 18. Tube side fluid enters the contactor via line 20 and passes through an inlet chamber 22 which distributes the fluid to the tube bundle 12. An outlet chamber 24 collects the tube side fluid which exits the contactor through a line 26.

Isoparaffins enter the process from a line 28 and are combined with recycled hydrocarbons from a line 30 in a drum 29. Line 32 carries the combined isoparaffinic feed into combination with an olefin feed entering the process via a line 34. The combined feedstream enters the contactor via line 36. The contactor also receives a flash recycle stream of hydrocarbons via a line 38 from a drum 56. Make-up acid for the process enters via a line 40 and is combined with recycle acid from an acid settler 42 that passes through a line 44. The combined acid stream enters contactor 10 via line 46. An additional flow of acid passes from an effluent settler 48 via a line 50 and into contactor 10.

An emulsion containing acid and alkylate product passes out of contactor 10 via a line 52 and into acid settler 42. A line 44 carries the emulsion over to the effluent settler 48. Alkylate product flows from the effluent settler and through the contactor via lines 57, 20 and 26 as previously described. In conventional cases the alkylate product which passes overhead from the settler 48 is expanded by passing through a control valve 59 before supplying the fluid through line 20. A restriction orifice 60 provides means for measuring the flow from line 57. Effluent from line 26 empties via line 62 into a trap defined by a partitioned portion of flash drum 56. A portion of the settler overhead effluent by-passes contactor 10 via line 58 and passes directly to the trap of the partitioned portion of drum 56 via line 62.

Vapor and liquid portions from line 62 are separated in the suction trap of drum 56. Line 64 carries liquid alkylate products over to a deisobutanizer 66 that separates alkylate products into a product stream 68 and returns feed isoparaffins, via a line 30, to drum 29 for recycle to the contactor.

Separated vapors and flash vapors from an economizer 88 of the compression section combine in the flash portion of suction drum 56 for withdrawal by line 70. Vapor from line 70 enters the suction side of a compressor 72 which raises the pressure of the vapor from line 70. An intermediate stage of compressor 72 receives an economizer vapor stream carried by line 74. The compressor pushes compressed vapors into a line 73 and through a condenser 76. Line 78 passes cooled vapors to an accumulator 80. Liquid from the accumulator, taken by line 82 and cooled by a condenser 84, passes via line 86 into economizer 88 that separates vapor for recycle to the intermediate stage of the compressor via line 74 and supplies the condensed hydrocarbon containing liquid carried by line 90 to drum 56. Vapors from accumulator 80 pass overhead via a line 92 and, typically, into a depropanizer.

In a typical acid catalyzed alkylation process the reactor effluent stream containing the alkylate product (shown as 57 in FIG. 1) is throttled from a pressure of about 60 to 70 psi to a pressure of about 5 to 50 psi. As a result of this Joule-Thomson expansion, the hydrocarbon liquid is cooled to between 30° to 40° F. and vapor is generated. Typically, this vapor will be in a range of between 3 to 10% by weight and 90 to 98% by volume. The two phase mixture of hydrocarbon liquid and vapor enters the tubes in the contactor which removes the heat generated by the alkylation reaction taking place on the shell side of the contactor.

The method of this invention is advantageously applied to the inlet chamber 22 of contactor 10. Inlet chamber 22 can contain a number of different distribution devices that will distribute the alkylate product entering the inlet of tube bundle 12.

Figure 2:
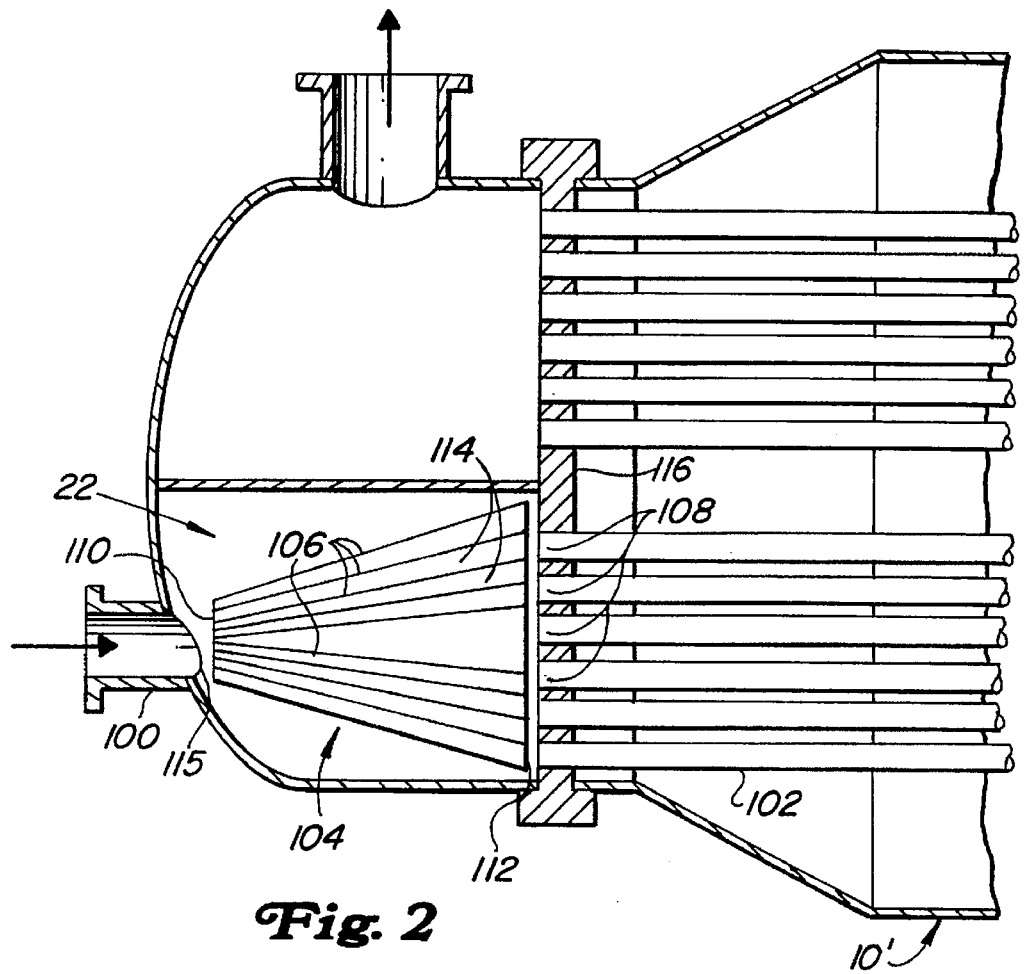
FIG. 2 is a schematic illustration of an exchanger incorporating a flow distributor of this invention.

FIG. 2 schematically shows the inlet and outlet portion for the tube side of a contactor 10' which is similar to the contactor 10. As compared to FIG. 1, FIG. 2 shows contactor 10' with a modified nozzle 100 having a center line parallel to the center line of heat exchange tubes 102. One method of dividing the flow through the inlet chamber in a manner to equalize the distribution of liquid and the ratio of liquid to vapor entering each tube is by using a two phase distributor as shown schematically in FIG. 2 by number 104. The distributor depicted in FIG. 2 consist of a series of concentric vanes 106. Vanes 106 define flow channels 114. The vanes are arranged to divide the flow entering nozzle 100 into a plurality of inlet streams that pass through flow channels 114 and are directed into the inlets 108 of the tubes 102. The vanes collectively define the cross sectional area of each of the flow channels at the inlet end 110 and the outlet end 112. The cross-sectional areas of the flow channels 114 at the inlet end 110 and the outlet end 112 are proportional to the number of tube inlets 108 into which each individual channel 114 directs its portion of the inlet stream. The inlet end 110 of the distributor 104 is located close to the outlet end 115 of nozzle 100. Similarly, the outlet of distributor 112 is located close to the tube inlets 108. The outer perimeter of distributor 104 at the outlet 112 will preferably match the outer periphery of tubes 102. Preferably, outlet end 112 is less than 1 inch from the tube sheet 116 containing the inlets 108 for tubes 102. The inlet end of distributor 110 will also have an outer periphery that closely matches the outer diameter of nozzle 100. Inlet end 110 for distributor 104 will also preferably have a location within 1 inch or less of the outlet end 115 of nozzle 100. It is also possible to extend inlet end 110 directly into nozzle 100 to insure a complete division of the fluid stream entering nozzle 100 into a plurality of inlet streams. The distributor 104 may be added during the initial fabrication of the contactor or retrofined into an existing contactor.

Figure 3:
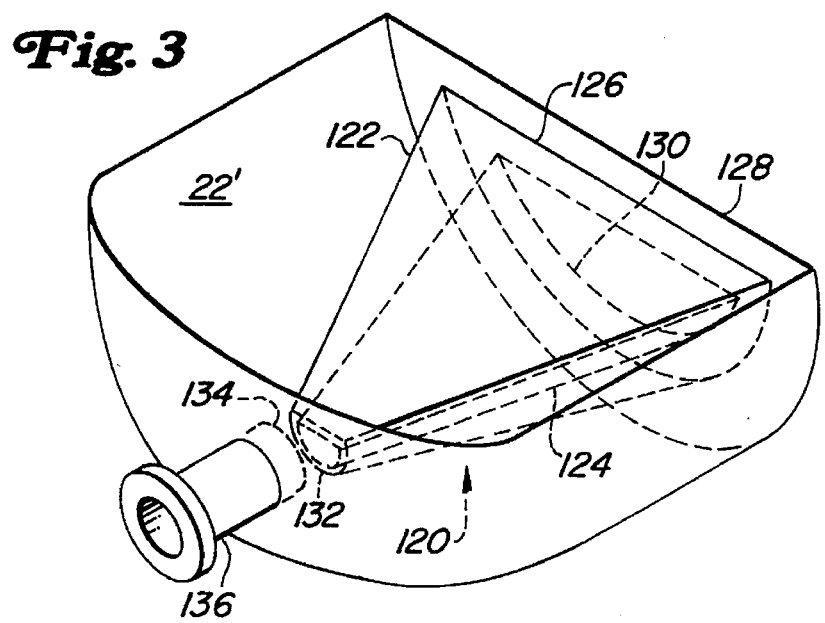
FIG. 3 shows a modified flow distributor of the type generally depicted in FIG. 2.

Effective arrangements of vanes within the inlet chamber 22 may take on a variety of forms. FIG. 3 shows a different arrangement for the vanes within an inlet chamber 22'. The vane arrangement 120 consists of an outer vane 122 and an inner vane 124. For simplicity the arrangement of FIG. 3 only shows two vanes, but other forms of the arrangement will preferably use additional vanes. An outlet end 126 of vane 124 has the same shape as the outlet end 128 of inlet chamber 22'. The outlet end 130 of inner vane 124 again has the same shape as the outlet end 128 of inlet chamber 22' and the outlet end 126. The outlet end 134 of a nozzle 136 feeds mixed phase fluid directly into the inlet end of distributor 120. The inner and outer vanes 124 and 122 define three flow channels into which the fluid stream entering via nozzle 136 is divided. The first fluid stream is that contained within inner vane 124. The second fluid inlet stream is contained between the outside of vane 124 and the inside of vane 122. The third flow channel is defined by the remaining interior of inlet chamber 22 that lies outside outer vane 122. The size of the openings for receiving fluid flow from outlet end 134 into and around the inlet 132 of distributor 120 is proportioned in accordance with the number of tube inlets served by each of the flow channels.

Successful operation of the vane-type distributors rely on a homogenous mixture of vapor and liquid entering via the nozzle that supplies fluid to the inlet chamber. In some cases, piping upstream of the inlet nozzle to the inlet chamber may cause separation of the liquid from the gas within the fluid as it passes out of the inlet nozzle. Where such localized maldistribution of fluid exiting the nozzle is expected, blending vanes or other mixing apparatus immediately upstream of the inlet nozzle will insure injection of a homogenous mixture of liquid and vapor into the inlet chamber.

The typical nozzle orientation for the contactor, as illustrated in FIGS. 1 and 4 by contactor 10, is radial. The radial inlet nozzle contributes substantially to the maldistribution of vapor and liquid as fluid flows into the contactor. Looking then at the enlarged detail of a contactor 10 using this invention, FIG. 4 depicts a radial inlet nozzle 140 that supplies a mixture of liquid and gas to a plurality of heat exchange tubes 102 via inlet chamber 22. The contactor of FIG. 4 uses a turning vane type distributor 142 to equalize the total liquid distribution and the proportion of liquid to vapor in the fluid supply to inlets 108 of tubes 102. The turning vane distributor consists of a series of curved vanes 144 that define flow channels 146 between the adjacent vanes. In the arrangement shown on FIG. 4, the vanes are not necessarily designed and spaced to provide equal flow areas or tube inlet areas proportional to flow in the passages between adjacent vanes, but are preferably arranged to result in equal pressure drop in the passage between any two vanes. This is due to the non-symmetrical flow path from the inlet nozzle to the tube created by the use of radial inlet nozzles wherein the tubes in the interior of the tube bundle have the greatest distance from the inlet nozzle. Thus, the vane supplying fluid to the interior tubes would require a larger spacing between the vanes in order to get the same flow as the tubes on the periphery of the tube bundle i.e., those tubes close to the bottom of the contactor shown in FIG. 4 where the distance from the nozzle to the tube sheet is much less. Therefore, placing the inlet 145 of the distributor close to the outlet of nozzle 140 divides the fluid into streams having equal ratios of liquid to vapor and sizing the channels for equal pressure drop insures that each tube inlet receives about the same amount of fluid.

A variety of inlet distributors can provide fluid flow from a radial inlet nozzle to the tubes. In place of the closed turning vane system shown in FIG. 4, the fluid flow into the inlet nozzle may be divided as shown in FIG. 5 into a plurality of streams by a cluster of small diameter tubes 147 that originate from a blind flange 149 at the inlet nozzle. These small diameter tubes can uniformly distribute the flow to all the tubes in the bundle. Various diameter tubes can be used to compensate for different flow lengths and thereby effectively equalize the pressure drop through all the distributor tubes. Thus the tubes create the plurality of differing inlet streams.

Another method of distributing fluid flow from a radial flow inlet nozzle to a vertical tube sheet is shown in FIG. 6. FIG. 6 shows an inlet chamber 22" sectioned by a baffle 148. A section 150 of the inlet chamber is filled with structured packing having a directional orientation. The packing distributes mixed phase fluid from an inlet nozzle 152 to inlets 108' of tubes 102'. The directional orientation of the structured packing turns the flow entering through nozzle 152 by 90° to direct a multiplicity of inlet streams created by the channels of the structured packing directly into inlets 108' of tubes 102'. Partition 148 further divides the volume of inlet chamber 22 to enhance the performance of the distribution device by reducing the overall volume of the inlet chamber.

This invention contemplates other methods than distributors for equalizing the liquid distribution and the ratio of liquid to vapor entering the inlets of the tubes. FIG. 7 shows such an arrangement wherein the fluid initially enters inlet chamber 22'" in liquid phase through a nozzle 154. Such an arrangement is particularly useful for an alkylation process where there is a chilling of the fluid entering the contactor by Joule-Thomson expansion. In conjunction with the arrangement shown in FIG. 7, the Joule-Thomson expansion is preferably not performed prior to fluid entering inlet chamber 22''' as previously described so that all of the fluid can enter the inlet chamber in a subcooled liquid phase. The inlet chamber has located within it a series of perforated plugs 156 located ahead of the inlets 108" of tubes 102". The plugs 156 can be located in the inlet chamber 22''' or extend into the tubes in which case the inlet chamber is considered to include the portion of the tube containing the plug and the inlet of the tube located after the outlet of the plug.

It is not necessary that all of the pressure drop associated with the Joule-Thomson expansion be taken across the plugs 156. A substantial portion of the pressure drop may still be effected over an expansion device such as control valve 59 (See FIG. 1 ). The advantages of liquid phase distribution may be obtained by only taking the final portion of the pressure drop across plugs 156. This final portion is that pressure drop over which there is a transition from a subcooled liquid to a two phase mixture. Typically the pressure drop associated with the transition is from about 5 to 15 psi.

FIG. 8 shows the plug arrangement in more detail. The plug 156 is located just ahead of the inlet portion 108" of the tube. Plug 156 has a shoulder 158 that abuts the tube sheet 116'. As liquid passes through restricted opening 160 and exits out of end 162 of the plug, the pressure drop induced by plug 156 causes the Joule-Thomson expansion of the liquid to occur just at the outlet of the plug. Therefore, the inlet chamber divides the liquid fluid evenly due to the pressure drop associated with each plug and each plug which comprises a portion of the inlet chamber forms separate streams having equal ratios of liquid to vapor in each of the tubes just as the fluid exits the inlet chamber.

EXAMPLES

The operation of reactor/contactors in an acid catalyzed reaction zone for the alkylation of hydrocarbons were measured, calculated and evaluated to determine the benefits provided by applying a distribution device. For a conventional bare tube reactor/contactor, the internal circulation rate of the hydrocarbon and acid emulsion on the shell side of the contactor is in a range of about 40,000 to 60,000 gallons per minute. The overall heat transfer coefficient of the contactor is from 35 to 55 BTU/HR-FT$^2$-°F. depending on the flow rate, and capacity. The corresponding emulsion heat transfer coefficient i.e., shell side heat transfer coefficient, of prior art reactor/contactors is about 90 to 150 BTU/HR-FT$^2$-°F.

Example 1

In order to show the surprising effect of distributing fluid in a manner to equalize liquid and vapor to the tubes within a reactor/contactor for the acid catalyzed alkylation of hydrocarbons, a series of field measurements were obtained and compared with known heat transfer correlations. Field measurements were taken from an acid catalyzed alkylation process using a contactor that operated at an internal circulation rate of 40,000 GPM on the emulsion side, i.e. shell side of the contactor, and at a viscosity of about 43 CP. Measurements determine that the average heat transfer coefficient across the tubes of the contactor was 48 BTU/HR-FT$^2$-°F. The corresponding shell side film heat transfer coefficient was determined using an experimental correlation to equal 136 BTU/HR-FT$^2$-°F.

Example 2

By dividing the fluid stream entering the contactor and equalizing the total liquid and the ratio of vapor and liquid in the fluid entering each of the tubes, the bare tube heat transfer coefficient can be improved. Based on calculation using known heat transfer correlations, the tube side boiling heat transfer coefficient for the bare tubes with a well distributed fluid was determined to be 325 BTU/HR-FT$^2$-°F. Overall heat transfer coefficients for the bare tubes can be increased to 70 BTU/HR-FT$^2$-°F. respectively. Therefore distribution means will improve the bare tube operation.

Example 3

Based on a tube side coefficient calculated from laboratory data and known heat transfer correlations, the calculated boiling coefficient on the tube side with enhanced nucleate boiling surface tubes was determined. With a well distributed fluid the tubes with the enhanced nucleate boiling surface will have a tube side heat transfer coefficient of 800 BTU/HR-FT$^2$-°F. By dividing the fluid stream entering the contactor and to evenly distribute liquid and equalizing the ratio of vapor and liquid in the fluid entering each of the tubes, the enhanced tube heat transfer coefficient will be greatly improved. The overall coefficient for the enhanced nucleate boiling surface tubes will increase to 84 BTU/HR-FT$^2$-°F. Therefore, although distribution means will improve the bare tube operation, more surprisingly the enhanced boiling surface has much more sensitivity to the control of liquid distribution and vapor to liquid ratios so that the application of distribution means provides an unexpectedly greater benefit.

The bare tube and the enhanced nucleate boiling surfaces both benefit from the distribution method of this invention. As the examples show, the bare tube and enhanced boiling surface tube performance are improved by factors of 1.46 and 1.75 respectively.

We claim:

1. In a process of alkylating isoparaffinic hydrocarbons with olefinic hydrocarbons in the presence of an acid catalyst comprising the steps of reacting isoparaffinic hydrocarbons and olefinic hydrocarbons in the presence of acid catalyst in a reaction zone to form alkylate, withdrawing a mixture of hydrocarbons with acid catalyst as effluent from said reaction zone, separating said effluent into an acid phase and a hydrocarbon phase in a first separating zone, reducing the pressure on the hydrocarbon phase to refrigerate it and vaporize volatile hydrocarbons, passing the refrigerated hydrocarbon phase into contact with a boiling surface located on the interior of a plurality of heat exchange tubes to effect indirect heat exchange with the reaction mixture of hydrocarbons and catalyst in the reaction zone and to remove exothermic heat of reaction and vaporize further volatile hydrocarbons in the hydrocarbon phase, separating the liquified portion of the hydrocarbon phase from the vapor portion thereof in a second separating zone, fractionating the liquid portion of the hydrocarbon phase to remove alkylate, passing the vapor phase material removed in said second separating zone through a compressor and a condenser to compress and condense the vapor phase to form a liquid phase, reducing the pressure on the liquid phase to refrigerate it and vaporize volatile hydrocarbons forming an isoparaffinic hydrocarbon liquid phase and a volatile hydrocarbon vapor phase, separating the refrigerated isoparaffinic hydrocarbon liquid phase from the volatile hydrocarbon vapor phase in a third separating zone, and adding the separated refrigerated isoparaffinic hydrocarbon liquid phase as a reactant in the reaction zone, the improvement which comprises:

passing the hydrocarbon phase to a tube inlet chamber that supplies said hydrocarbon phase to said plurality of heat exchange tubes;

dividing said hydrocarbon phase in said chamber into a plurality of inlet streams in a manner to equalize any weight ratio of liquid to vapor and the total liquid distribution of each of said streams; and, directing each of said inlet streams into an inlet of one or more of said heat exchange tubes.

2. The improvement of claim 1 wherein the vapor to liquid ratio and the amount of liquid of each of said inlet streams varies by no more than 20%.

3. The improvement of claim 1 wherein each of said inlet streams directs fluid into the inlet of more than one of said heat exchange tubes.

4. The improvement of claim 1 wherein the boiling surface is an enhanced boiling surface comprising a porous boiling layer.

5. The improvement of claim 1 wherein a pressure drop at the inlet of each tube divides said hydrocarbon phase in said manner to equalize the weight ratio of vapor to liquid of each of said inlet streams.

6. The improvement of claim 5 wherein said hydrocarbon phase enters said chamber as liquid.

7. The improvement of claim 1 wherein said hydrocarbon phase passes through said tubes at a mass rate of 100 to 400 lb/hr and said tubes have an outside diameter of from ¾ to 1 inch.

8. In a process of alkylating isoparaffinic hydrocarbons with olefinic hydrocarbons in the presence of an acid catalyst comprising the steps of reacting isoparaffinic hydrocarbons and olefinic hydrocarbons in the presence of acid catalyst in a reaction zone to form alkylate, withdrawing a mixture of hydrocarbons with acid catalyst as effluent from said reaction zone, separating said effluent into an acid phase and a hydrocarbon phase in a first separating zone, reducing the pressure on the hydrocarbon phase to refrigerate it and vaporize volatile hydrocarbons, passing the refrigerated hydrocarbon phase into contact with a boiling surface located on the interior of a plurality of heat exchange tubes to effect indirect heat exchange with the reaction mixture of hydrocarbons and catalyst in the reaction zone and to remove exothermic heat of reaction and vaporize further volatile hydrocarbons in the hydrocarbon phase, separating the liquified portion of the hydrocarbon phase from the vapor portion thereof in a second separating zone, fractionating the liquid portion of the hydrocarbon phase to remove alkylate, passing the vapor phase material removed in said second separating zone through a compressor and a condenser to compress and condense the vapor phase to form a liquid phase, reducing the pressure on the liquid phase to refrigerate it and vaporize volatile hydrocarbons forming an isoparaffinic hydrocarbon liquid phase and a volatile hydrocarbon vapor phase, separating the refrigerated isoparaffinic hydrocarbon liquid phase from the volatile hydrocarbon vapor phase in a third separating zone, and adding the separated refrigerated isoparaffinic hydrocarbon liquid phase as a reactant in the reaction zone, the improvement which comprises:

passing the hydrocarbon phase in a liquid phase to a tube inlet chamber that supplies said hydrocarbon phase to said plurality of heat exchange tubes;

dividing said hydrocarbon phase in said chamber into a plurality of inlet streams and providing a pressure drop at the inlet of each tube that divides the hydrocarbon phase in a manner to equalize the weight ratio of vapor to liquid of each of said inlet streams and flashes said liquid phase to produce a mixed phase stream; and, directing each of said inlet streams into an inlet of one or more of said heat exchange tubes.

* * * * *